(12) United States Patent
Benedini et al.

(10) Patent No.: US 6,700,011 B1
(45) Date of Patent: Mar. 2, 2004

(54) PROCESS FOR THE PREPARATION OF NAPROXENE NITROXYALKYLESTERS

(75) Inventors: Francesca Benedini, Milan (IT); Erminio Oldani, Milan (IT); Graziano Castaldi, Novara (IT); Antonio Tarquini, Alessandria (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 10/031,412

(22) PCT Filed: Jul. 27, 2000

(86) PCT No.: PCT/EP00/07222

§ 371 (c)(1),
(2), (4) Date: Jan. 18, 2002

(87) PCT Pub. No.: WO01/10814

PCT Pub. Date: Feb. 15, 2001

(30) Foreign Application Priority Data

Aug. 4, 1999 (IT) .......................... MI99A1753

(51) Int. Cl.[7] ............................. C07C 203/04
(52) U.S. Cl. ....................................... 558/482
(58) Field of Search ......................... 558/482

(56) References Cited

U.S. PATENT DOCUMENTS 5,700,947 A  * 12/1997  Soldato ...................... 548/491

FOREIGN PATENT DOCUMENTS

| FR | 2 757 159 A | 6/1998 |
| WO | WO 92/01668 A | 2/1992 |
| WO | WO 95/09831 A | 4/1995 |
| WO | WO 95/30641 A | 11/1995 |
| WO | WO 97/16405 A | 5/1997 |
| WO | WO 98/25918 | 6/1998 |

* cited by examiner

Primary Examiner—Joseph K. McKane
Assistant Examiner—Ebenezer Sackey
(74) Attorney, Agent, or Firm—Arent Fox Kintner Plotkin & Kahn PLLC

(57) ABSTRACT

A process for obtaining nitroxyalkylesters of the 2-(S)-(6-methoxy-2-naphthyl)-propanoic acid having an enantiomeric excess higher than or equal to 95%, preferably higher than or equal to 98%, characterized in that an halide of the 2-(S)-(6-methoxy-2-naphthyl)-propanoic acid of formula A-Hal, wherein A is the acid acyl residue, is reacted in an inert organic solvent with an aliphatic nitroxyalkanol HO—Y—ONO$_2$, wherein Y is a $C_2$–$C_{20}$ alkylene or a cycloalkylene from 3 to 8 carbon atoms, or an alkylene as defined containing a cycloalkylene as defined, in the presence of an inorganic base.

5 Claims, No Drawings

PROCESS FOR THE PREPARATION OF NAPROXENE NITROXYALKYLESTERS

This application is a 371 of PCT/EP00/07222 filed on Jul. 27, 2000.

The present invention relates to a new method for preparing nitroxyalkylesters of the 2-(S)-(6-methoxy-2-naphthyl)-propanoic acid (naproxene) having an enantiomeric excess of the (S) form higher than or equal to 97%, preferably higher than or equal to 98%, combined with high yields, higher than 75–80%, preferably higher than 85%.

It is well known in the prior art that the enantiomeric form (S) is the active form from the pharmacological point of view of the above mentioned product.

In the prior art synthesis methods of nitroxyalkylesters of the 2-(S)-(6-methoxy-2-naphthyl)-propanoic acid, are known. In the patent application WO 98/25,918, a synthesis method of naproxene nitroxyalkyl esters containing in the alkyl chain a saturated $C_3$–$C_8$ cycloalkyl residue, is described. In said process the acid or one of its functional derivatives, for example, chloride or anhydride, is reacted, in an inert organic solvent, with a nitroalkanol containing a cycloalkyl residue as above defined. The reaction takes place in the presence of an organic nitrogenated base, such as for example 4-dimethyl aminopyridine, morpholine, N-methyl morpholine or triethylamine. Tests carried out by the Applicant have shown that this process of the prior art does not allow to obtain naproxene nitroxyalkylesters having an enantiomeric excess in the range of 55–80%, only with a specific organic base, 4-N,N-dimethylamino pyridine, 94% is obtained.

The need was therefore felt to obtain naproxene nitroxyalkylesters having an higher enantiomeric excess, at least of 97%, preferably equal to or higher than 98%.

An object of the present invention is a process to obtain nitroxyalkylesters of the 2-(S)-(6-methoxy-2-naphthyl)-propanoic acid having an enantiomeric excess higher than or equal to 97%, preferably higher than or equal to 98%, characterized in that an halide of the 2-(S)-(6-methoxy-2-naphthyl)-propanoic acid of formula A-Hal, wherein A is the acylic residue of said acid, is reacted in an inert organic solvent with an aliphatic nitroxyalkanol HO—Y—$ONO_2$, wherein Y has one of the following meanings:

a linear or optionally branched $C_1$–$C_{20}$, preferably $C_2$–$C_5$, alkylene;

a cycloalkylene with ring from 3 to 8 carbon atoms, preferably from 5 to 7 carbon atoms, said cycloalkylene optionally can be substituted with one or two alkylenes as above defined, and/or with one or more alkyl radicals having in the chain a number of carbon atoms as above defined for alkylene;

an aromatic residue with ring having 5 or 6 carbon atoms, said aromatic residue optionally can be substituted with one or two alkylenes as above defined, and/or with one or more alkyl radicals having in the chain a number of carbon atoms as above defined for alkylene, or a —COOH group;

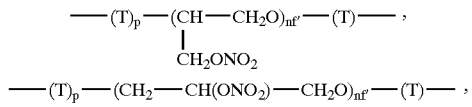

T being alkylene as above defined and p an integer equal to zero or one, alkylene having the above mentioned meaning, nf is an integer from 1 to 6, preferably from 1 to 4; in the presence of an inorganic base, to give the corresponding nitroxyalkylester of the 2-(S)-(6-methoxy-2-naphthyl)-propanoic acid of formula A—O—Y—$ONO_2$, wherein A and Y are as above defined.

Y can also be a combination of two or more of the mentioned group.

The aliphatic nitroxyalcohol amount on molar basis is in the range 1–2, preferablyl 1.2–1.5, with respect to that of the acid halide.

With inorganic bases hydroxides, oxides, carbonates and bicarbonates, silicates, aluminosilicates of the alkaline and alkaline-earth metals, or hydroxides, oxides, carbonates and bicarbonates of metals belonging to the group IIB, preferably zinc, or to groups IIIa or IVa, preferably tin, are meant.

The inorganic base amount is in molar ratio with the acid halide amount generally in the range 1–2, preferably 1.2–1.5.

With inert organic solvent according to the present invention aromatic hydrocarbons are meant, such as for example toluene and xylene, chlorinated or fluorinated organic solvents, for example methylene chloride, chlorobenzene, aliphatic esters for example $C_1$–$C_4$ acids esters with $C_1$–$C_5$ alcohols such as for example ethyl acetate and butyl acetate, etc.

The solvent amount is not critical and generally from 1 to 10 volumes of solvent are used, preferabaly from 2 to 5 volumes based on the acid halide weight.

The reaction is carried out at a temperature in the range –20° C. and 50° C., preferably 0° C. and 20° C.

The nitroxyalkylesters of the 2-(S)-(6-methoxy-2-naphthyl)-propanoic acid are recovered at the end of the reaction, after addition of water to the organic phase, separation of the phases and solvent evaporation. If necessary, a further purification can be carried out by chromatography on silica gel, column in order to increase the product titre.

Alternatively, the compound can also be purified by crystallization from a suitable solvent.

Aliphatic nitroxyalcohols can be prepared according to the known methods in the prior art. See for example Gazzetta Chim. It. 1987, 117, 173 and WO 98/25,918.

The Applicant has found that surprisingly by the use of inorganic bases it is possible to improve the enantiomeric excess of naproxene nitroxyalkylesters with respect to the prior art methods, which use, as seen, organic bases, with high yields as above mentioned.

The following examples have the purpose to illustrate the invention and they are not to be intended as limitative thereof.

EXAMPLE 1 (COMPARATIVE)

Preparation of 4-Nitroxybutyl Ester of the 2-(S)-(6-Methoxy-2-naphthyl)-propanoic Acid According to WO 98/25918

A mixture of the 2-(S)-(6-methoxy-2-naphthyl)-propanoic acid (0.32 g, 1.4 mmoles), 4-N,N-dimethylamino pyridine (16 mg, 0.13 mmoles), 4-nitroxybutan-1-ol (0.34 g, 2.5 mmoles) in dichloromethane (6 ml) at a temperature in the range 0° C.–5° C. is added, under stirring, to a solution of N,N'-dicyclohexylcarbodiimide (0.29 g, 1.4 mmoles) in dichloromethane (6 ml). The mixture is left under stirring at the same temperature for 3 hours and then dried by solvent evaporation under vacuum. The residue is purified by chromatography on silica gel column (eluent dichloromethane) to give the 4-nitroxybutyl ester of the 2-(S)-(6-methoxy-2-naphthyl)-propanoic acid (0.41 g, 1.19 mmoles), yield 85%) in the form of an oil. HPLC purity: 98%.

$^1$H NMR(CDCl$_3$) δ (ppm): 1.59 (d, 3H, J=7.5 Hz); 1.65 (m, 4H); 3.85 (q, 1H, J=7.5 Hz); 3.91 (m, 2H); 4.10 (m, 2H); 7.1–7.7 (m, aromatic, 8H). Enantiomeric excess: 94%.

EXAMPLE 2

To a solution of 4-nitroxybutan-1-ol (2.0 g; 14.8 mmoles) in dichloromethane (20 ml), cooled at 0° C.–5° C., potassium carbonate (3.21 g, 23.2 mmoles) is added under stirring.

To the mixture a solution of 2-(S)-(6-methoxy-2-naphthyl)-propanoic acid chloride (3.86 g, 15.5 mmoles; enantiomeric excess 98%) in dichloromethane (22 ml) is added, maintaining the temperature in the range 10° C.–15° C. When the addition is over the temperature is increased and maintained for 10 hours at a value in the range 15° C.–20° C. and then the solution is filtered. The solvent is evaporated under vacuum. The residue is purified by chromatography on silica gel column (eluent dichloromethane) to give the 4-nitroxybutyl ester of the 2-(S)-(6-methoxy-2-naphthyl)-propanoic acid (4.4 g, 12.6 mmoles, yield 85%) in the form of an oil. HPLC purity: 99%.

$^1$H NMR(CDCl$_3$) δ (ppm): 1.59 (d, 3H, J=7.5 Hz); 1.65 (m, 4H); 3.85 (q, 1H, J=7.5 Hz); 3.91 (m, 2H); 4.10 (m, 2H); 7.1–7.7 (m, aromatic, 8H). Enantiomeric excess: 98%.

EXAMPLE 3

Example 2 is repeated using toluene as solvent. The nitroxyester yield is 76%, the (HPLC) purity >99%. The enatiomeric excess is equal to 98%.

EXAMPLE 4

Example 2 is repeated but using as a base calcium carbonate. 4.6 g, equal to 13.3 mmoles of nitroxyester (yield 90%) are obtained, HPLC purity >99%, enantiomeric excess 98%.

EXAMPLE 5

Example 2 is repeated but using as a base calcium alumino-silicate. 4.6 g, equal to 13.3 mmoles of nitroxyester (yield 90%) are obtained, HPLC purity >99%, enantiomeric excess 98%.

EXAMPLE 6

To a solution of 4-nitroxybutan-1-ol (2.0 g; 14.8 mmoles) in dichloromethane (20 ml), cooled at a temperature in the range 0° C.–5° C., potassium carbonate (3.21 g, 23.2 mmoles) is added under stirring.

To the mixture a solution of 2-(S)-(6-methoxy-2-naphthyl)-propanoic acid chloride (3.86 g. 15.5 mmoles, enantidmeric excess 98%) in dichloromethane (22 ml) is added, maintaining the temperature in the range 10° C.–15° C. When the addition is over, the temperature is increased to a value in the range 15° C.–20° C. for 10 hours and then the solution is filtered. Water (1 ml) and N,N-dimethylformamide (2 ml) are added to the solution and left under stirring at room temperature for 3 hours. At the end the organic phase is separated, washed with water and filtered through a potassium carbonate panel. The solvent is evaporated under vacuum and 4.1 g, equivalent to 11.8 mmoles of ester (yield 80%) in the form of an oil, are obtained, HPLC purity >99%, enantiomeric excess 98%.

EXAMPLE 7 (COMPARATIVE)

Example 2 is repeated but using as a base triethylamine. The obtained mixture after the reaction is analyzed to evaluate the enantiomeric excess, which results equal to 80%.

EXAMPLE 8 (COMPARATIVE)

Example 2 is repeated but using as a base diisopropyl-ethylamine. The mixture obtained after the reaction is analyzed to evaluate the enantiomeric excess, which results equal to 76%.

EXAMPLE 9 (COMPARATIVE)

Example 2 is repeated but using as a base N-methylmorpholine. The mixture obtained after the reaction is analyzed to evaluate the enantiomeric excess, which results equal to 56%.

What is claimed is:

1. A process for obtaining nitroxyalkylesters of the 2-(S)-(6-methoxy-2-naphthyl)-propanoic acid having an enantomeric excess higher than or equal to 97%, characterized in that an acyl halide of 2-(S)-(6-methoxy-2-naphthyl)-propanoic acid is reacted in an inert organic solvent with an aliphatic nitroxylakanol HO—Y—ONO$_2$, wherein Y has one of the following meanings:

a linear or optionally branched $C_1$–$C_{20}$ alkylene, or a cycloalkylene with ring from 3 to 8 carbon atoms, said cycloalkylene optionally substituted with one or two alkylenes as above defined, and/or with one or more alkyl radicals having in the chain a number of carbon atoms as above defined for alkylene;

an aromatic group with ring having 5 or 6 carbon atoms, said aromatic group optionally substituted with one or two alkylenes as above defined, and/or with one or more alkyl radicals having in the chain a number of carbon atoms as above defined for alkylene, or a —COOH group;

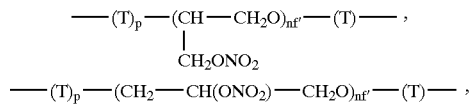

T being alkylene as above defined and p an integer equal to zero or one, alkylene having the above mentioned meaning, nf' is an integer from 1 to 6; in the presence of an inorganic base, to give the corresponding nitroxyalkylester of the 2-(S)-(6-methoxy-2-naphthyl)-propanoic acid of formula Acyl-O—Y—ONO$_2$, wherein Y is as above defined.

2. A process according to claim 1, wherein the aliphatic nitroxyalcohol amount on a molar basis is in the range 1–2, with respect to that of the acid halide.

3. A process according to claim 1, wherein the inorganic bases are hydroxides, oxides, carbonates and bicarbonates, silicates, aluminosilicates of the alkaline and alkaline-earth metals, or hydroxides, oxides, carbonates and bicarbonates of metals belonging to the group IIB, or to groups IIIa or IVa.

4. A process according to claim 1, wherein the inorganic base amount is in a molar ratio with the acid halide amount in the range 1–2.

5. A process according to claim 1, wherein the reaction is carried out at a temperature in the range –20° C. and 50° C.

* * * * *